United States Patent
Matsuzawa et al.

(10) Patent No.: US 6,844,163 B1
(45) Date of Patent: Jan. 18, 2005

(54) METHOD FOR ANALYZING THE AMOUNT OF INTRAABDOMINAL ADIPOSE TISSUE

(75) Inventors: Yuji Matsuzawa, Takarazuka (JP); Hiroko Murakami, Ashiya (JP); Masako Nishizawa, Takarazuka (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/958,561
(22) PCT Filed: Apr. 6, 2000
(86) PCT No.: PCT/JP00/02210
§ 371 (c)(1), (2), (4) Date: Oct. 10, 2001
(87) PCT Pub. No.: WO00/62073
PCT Pub. Date: Oct. 19, 2000

(30) Foreign Application Priority Data

Apr. 12, 1999 (JP) .......................................... 11-103858

(51) Int. Cl.[7] .............................................. G01N 33/53
(52) U.S. Cl. ........................ 435/7.1; 435/7.21; 436/518; 530/350; 530/387.9
(58) Field of Search ................................ 435/7.1, 7.92; 436/518; 424/572, 574, 520

(56) References Cited

U.S. PATENT DOCUMENTS

| | | | |
|---|---|---|---|
| 4,376,110 A | 3/1983 | David et al. | |
| 4,952,496 A | 8/1990 | Studier et al. | |
| 5,693,489 A | 12/1997 | Studier et al. | |
| 5,874,399 A | * 2/1999 | Samal | 514/2 |

FOREIGN PATENT DOCUMENTS

| | | |
|---|---|---|
| EP | 0 601 360 A | 6/1994 |
| GB | 2074727 | 11/1981 |
| JP | 2-39747 | 9/1990 |
| WO | 96/05861 | 2/1996 |

OTHER PUBLICATIONS

Racette et al, Leptin production during moderate-intensity aerobic exercise, Jul. 1997, Journal of Clinical Endocrinology and Metabolism, vol. 82, No. 7, pp. 2275–7.*

Samal et al., Molecular and Cellular Biology, vol. 14, No. 2 (1994) pp. 1431–1437.

Arita, Y. et al.: "Paradoxical Decrease of an adipose–Specific Protein, Adiponection, in Obesity" Biochemical and Biolphysical Research Communications, vol. 257, Apr. 2, 1999, pp. 79–83, XP000867719.

(List continued on next page.)

*Primary Examiner*—Long V. Le
*Assistant Examiner*—Deborah A Davis
(74) *Attorney, Agent, or Firm*—Birch, Stewart, Kolasch & Birch, LLP

(57) ABSTRACT

The present invention provides a method for analyzing the amount of intraabdominal adipose tissue comprising:

determining the amount of intraabdominal tissue in a test-animal from the concentration of a protein in a body fluid, tissue or cell of said test-animal or in a prepared test solution from the body fluid, tissue or cell of said test-animal, based on the positive relationship between the amount of the intraabdominal adipose tissue in an animal and the concentration of a protein in a body fluid, tissue or cell of said animal or in a prepared solution from the body fluid, tissue or cell of said animal, wherein the protein is (1) encompassed by the amino acid sequence shown in SEQ ID NO:1 or is (2) recognized by an antibody against a protein encompassed by the amino acid sequence shown in SEQ ID NO:1.

13 Claims, 4 Drawing Sheets

OTHER PUBLICATIONS

Kazuhisa, M. et al.: "Analysis of an expression profile of genes in the human adipose tissue" GENE, vol. 190, 1997, pp. 227–235, XP004068379.

Samal, B. et al.: "Cloning and Characterization of the cDNA Encoding a Novel Human Pre–B–Cell Colony–Enhancing Factor" Molecular and Cellular Biology, vol. 14, No. 2, Feb. 1994, pp. 1431–1437, XP000933856.

Ahmed H Kissebah et al., Journal of Clinical Endocrinology and Metabolism, vol. 54, No. 2, (1982).

Tichiro Shimomura et al., Nature Medicine, vol. 2, No. 7, (Jul. 1996).

Constantine TSIGOS et al., $8^{th}$ European Congress on Obesity, (1997).

* cited by examiner

6,844,163 B1

METHOD FOR ANALYZING THE AMOUNT OF INTRAABDOMINAL ADIPOSE TISSUE

This application is the national phase under 35 U.S.C. § 371 of PCT International Application No. PCT/JP00/02210 which has an International filing date of Apr. 6, 2000, which designated the United States of America and was published in English.

BACKGROUND OF THE INVENTION

1. Field of the Invention

The present invention relates to a method for analyzing the amount of intraabdominal adipose tissue and its uses.

2. Description of the Related Art

Recently, it was revealed that the increase of adipose tissue in the peritoneal cavity, particularly the increase of adipose tissue by accumulating fat into adipose tissue which is present around vessels flowing in the portal veins, such as mesenteric adipose tissue or omental adipose tissue, is related closely to the onset of diseases including metabolic disorders such as diabetes, hyperlipemia and arteriosclerosis as well as cardiac vessel disorders such as coronary artery diseases, angina and myocardial infarction ("Naizo Shibogata Himan (Visceral Fatty-Type Obesity)", 1995, published by Iyaku Journal Ltd.). In order to predict the risk of onset of such diseases, there is a need for the development of an analytical method which can easily and rapidly manage the amount of intraabdominal adipose tissue.

As a method for analyzing the amount of intraabdominal adipose tissue, a method for estimating a waist/hip peripheral diameter ratio (W/H ratio) as an indicator (J. Clin. Endocrinol. Metab., vol. 54, p. 254, 1982) has been reported, but the W/H ratio provides a rough estimate of the amount of fat in the whole abdomen area and thus cannot clearly distinguish the amount of subcutaneous adipose tissue from the amount of intraabdominal adipose tissue. Accordingly, the method for estimating the amount of intraabdominal adipose tissue by using the W/H ratio as an indicator fails to be satisfactorily accurate and is inadequate as a method for analyzing the amount of intraabdominal adipose tissue.

SUMMARY OF THE INVENTION

Accordingly, there is demand to develop an analytical method which can easily and rapidly manage with satisfactory accuracy, the amount of intraabdominal adipose tissue.

As a result of studying under these circumstances and thereby arriving at the present invention, the present Inventors have found that there is a direct relationship or positive correlation between the concentration of a certain protein in blood and the area of intraabdominal adipose tissue in a section of the abdomen. As such, the amount of intraabdominal adipose tissue can be determined, based on the concentration of said protein.

That is, the present invention provides:

1. a method for analyzing the amount of intraabdominal adipose tissue comprising:
determining the amount of intraabdominal tissue in a test-animal from the concentration of a protein in a body fluid, tissue or cell of said test-animal or in a prepared test solution from the body fluid, tissue or cell of said test-animal, based on the positive relationship between the amount of the intraabdominal adipose tissue in an animal and the concentration of the protein in a body fluid, tissue or cell of said animal or in a prepared control solution from the body fluid, tissue or cell of said animal,
wherein the protein is (1) encompassed by the amino acid sequence shown in SEQ ID NO:1 or is (2) recognized by an antibody against a protein encompassed by the amino acid sequence shown in SEQ ID NO:1.

2. a method according to the above 1, wherein the amount of intraabdominal adipose tissue is the area of intraabdominal adipose tissue in a section of the abdomen.

3. a method according to the above 1, wherein the relationship is expressed as a linear function of a correlative function.

4. a method according to the above 1, wherein an immunochemical analysis determines the concentration of the protein in the body fluid tissue or cell of the animal or in a prepared solution from the body fluid, tissue or cell of said animal.

5. a method for analyzing intraabdominal adipose tissue comprising: determining the amount of intraabdominal adipose tissue in a test-animal from the concentration of a protein in a body fluid, tissue or cell of said test-animal or in a prepared solution from the body fluid, tissue or cell of said test-animal,
wherein the protein is (1) encompassed by the amino acid sequence shown in SEQ ID NO:1 or is (2) recognized by an antibody against a protein encompassed by the amino acid sequence shown in SEQ ID NO:1.

6. a method according to the above 1 or 5, wherein an immunochemical analysis determines the concentration of the protein in the body fluid, tissue or cell of said test-animal or in a prepared solution from the body fluid, tissue or cell of said test-animal.

7. a method according to the above 1 or 5, wherein the test-animal is a mammal.

8. a method according to the above 1, 2, 3, 4, 5 or 6, wherein the body fluid, tissue or cell of said test-animal or the prepared test solution from the body fluid, tissue or cell of said test-animal is blood.

9. an examination method comprising: predicting the risk of onset of a disease closely related to the amount of intraabdominal adipose tissue or judging the recovery of said disease in an individual, based on examining the increasing or decreasing amount of intraabdominal adipose tissue of said individual for a predetermined period by the method of any one of the above 1 to 8.

10. an examination method comprising:
predicting the risk of onset of a disease closely related to the amount of intraabdominal adipose tissue or judging the recovery of a disease in an individual of a test-animal, based on examining the increasing or decreasing concentration of a protein in a body fluid, tissue or cell of said test-animal or in a prepared test solution from the body fluid, tissue or cell of said test-animal, for a predetermined period,
wherein the protein is (1) encompassed by the amino acid sequence shown in SEQ ID NO:1 or is (2) recognized by an antibody against a protein encompassed by the amino acid sequence shown in SEQ ID NO:1.

11. an examination method comprising:
determining the amount of intraabdominal tissue in a test-animal with a method of any one of the above 1 to 8;
comparing the amount of intraabdominal adipose tissue in said test-animal to the amount of intraabdominal adipose tissue in a healthy animal of the same species of said test-animal; and
predicting the risk of onset of a disease closely related to the amount of intraabdominal adipose tissue or judging the recovery of a disease in said test-animal.

12. an examination method comprising:
determining the concentration of a protein in a body fluid, tissue or cell of a test-animal or in a prepared test solution from the body fluid, tissue or cell of said test-animal;

comparing the concentration of the protein in said test-animal to the concentration of the protein in a healthy animal of the same species of said test-animal; and predicting the risk of onset of a disease closely related to the amount of intraabdominal adipose tissue or judging the recovery of a disease in said test-animal, wherein the protein is (1) encompassed by the amino acid sequence shown in SEQ ID NO:1 or is (2) recognized by an antibody against a protein encompassed by the amino acid sequence shown in SEQ ID NO:1.

13. use of a protein for analyzing the amount of intraabdominal adipose tissue, wherein the protein is (1) encompassed by the amino acid sequence shown in SEQ ID NO:1 or is (2) recognized by an antibody against a protein encompassed by the amino acid sequence shown in SEQ ID NO:1.

14. a function expressing the positive relationship between the amount of intraabdominal adipose tissue in an animal and the concentration of a protein in a body fluid, tissue or cell of said test-animal or in a prepared test solution from the body fluid, tissue or cell of said test-animal, wherein the protein is (1) encompassed by the amino acid sequence shown in SEQ ID NO:1 or is (2) recognized by an antibody against a protein encompassed by the amino acid sequence shown in SEQ ID NO:1.

15. a kit comprising as a standard for analyzing the amount of intraabdominal adipose tissue in an animal, a protein encompassed by the amino acid sequence shown in SEQ ID NO:1 or recognized by an antibody against a protein encompassed by the amino acid sequence of SEQ ID NO:1.

16. a kit according to the above 15, further comprising an antibody recognizing a protein encompassed by the amino acid sequence shown in SEQ ID NO:1.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or step but not the exclusion of any other integer or step or group of integers or steps.

DETAILED DESCRIPTION OF THE INVENTION

Figure 1:
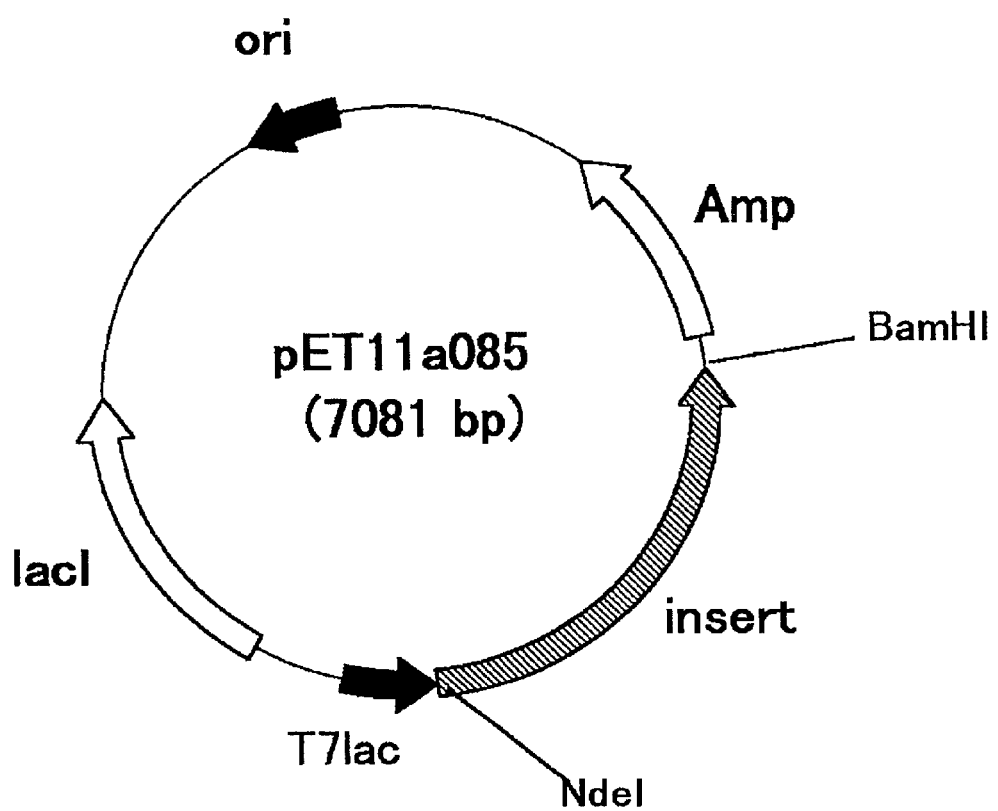
FIG. 1 shows the structure of expression plasmid pET11a085 for expressing in *E. coli*, a protein consisting of an amino acid sequence starting at the 27-position in the amino acid sequence shown in SEQ ID NO:1. The shaded portion in the drawing shows the insert coding for the protein to be expressed.

Hereinafter, the present invention is described in detail.

In the present invention, the "amount of intraabdominal adipose tissue" refers to the amount of adipose tissue in the abdominal rectus, external and internal abdominal oblique muscles, abdominal transverse, quadrate lumbar muscle, psoas major and inner portions of pyramid. As such, the amount of intraabdominal adipose tissue may employ the total amount (e.g. volume or weight) of intraabdominal adipose tissue or the area of intraabdominal adipose tissue in a section of the abdomen, which is known to be proportional to the total amount of intraabdominal adipose tissue (Int. J. Obesity, vol. 17, p. 187, 1993). The "area of intraabdominal adipose tissue in a section of the abdomen" refers to the area occupied by adipose tissue in the abdomen, that is, in the abdominal rectus, external and internal abdominal oblique muscle, abdominal transverse, quadrate lumbar muscle, psoas major and pyramid, which is discerned in a taken picture of the section of the abdomen, obtained in methods described in "Image Analysis Viewed from Symptoms" (compiled by the Japan Medical Association), such as computed tomography (referred to hereinafter as CT scanning) (Visceral Fatty-Type Obesity, 1995, published by Iyaku Journal Ltd.), ultrasound examination and magnetic resonance imaging. The term "abdomen" or "abdominal" refers to an area which is usually examined for measuring the area of intraabdominal adipose tissue, and roughly speaking, this site is typically above the groin and below the midriff forming a boundary with the chest.

The protein used in the analytical method of the present invention typically is a protein encompassed by the amino acid sequence shown in SEQ ID NO:1 or protein recognized by an antibody against said protein (hereinafter, such proteins are collectively referred to as the protein of the present invention). More specific examples of the protein of the present invention include a protein encompassed by the amino acid sequence shown in SEQ ID NO:1, as well as proteins which are recognized by an antibody against a protein encompassed by the amino acid sequence shown in SEQ ID NO:1. The latter protein may be, for example, proteins encompassed by the amino acid sequence shown in SEQ ID NO:1, wherein one or more amino acids have been deleted, replaced or added. The amino acid sequences wherein "amino acids have been deleted, replaced or added" typically include naturally occurring variations of a protein encompassed by the amino acid sequence shown in SEQ ID NO:1 e.g. resulting from intracellular processing or a difference in the type of species, a difference among individuals or tissues from which said protein was derived.

In order to analyze the amount of intraabdominal adipose tissue in a test-animal according to the present invention, based on the relationship between the concentration of the protein of the present invention in a body fluid, tissue or cell from an animal, preferably an animal which is of the same species as the test-animal, or in a prepared solution from the body fluid, tissue or cell of such an animal and the amount of intraabdominal adipose tissue in such an animal, the amount of intraabdominal adipose tissue in the test-animal is usually determined from the concentration of the protein of the present invention in a body fluid, tissue or cell of the test-animal or in a prepared test solution from the body fluid, tissue or cell of said test-animal. The body fluids from an animal include e.g. blood, urine, saliva etc.; the tissues therefrom include e.g. intraabdominal adipose tissue such as mesenteric adipose tissue and omental adipose tissue; and the cells therefrom include e.g. fat cells present in intraabdominal adipose tissue such as mesenteric adipose tissue and omental adipose tissue. Among the above-described body fluids, tissues and cells of an animal, blood may be mentioned as a preferable example. Further, a control solution or a test solution may be prepared by subjecting the body fluids, tissues and cells from an animal to post-treatment such as disruption treatments which use a crushing device such as a Teflon homogenizer or solid removing treatments which use a centrifuge, if so desired.

The relationship between the concentration of the protein of the present invention in body fluids, tissues or cells of an animal or in a prepared solution from the body fluids, tissues or cells of said animal and the amount of intraabdominal adipose tissue in said animal may be determined, for example, as follows: The concentration(s) of the protein of the present invention in a control solution from a control-animal, preferably in control solutions from plural individuals of a control-animal of a single species is determined by e.g. an immunochemical analysis described below. After the concentration of the protein of the present invention in the control solution is determined, the amount of intraabdominal adipose tissue in each of the animals may be determined as e.g. the area of intraabdominal adipose tissue in a section of the abdomen. For quantifying such an area, techniques such as CT scanning, ultrasound examination and magnetic resonance imaging are typically used. More specifically, photographing a section of the abdomen by CT scanning may be conducted according to a method described in "Visceral Fatty-Type Obesity" published in 1995 by Iyaku Journal Ltd. The area to be subjected to photographing a section of the abdomen is an area which is ordinarily measured for examining the amount of intraabdominal adipose tissue and which can provide for an accurate examination of the amount of the intraabdominal adipose tissue, and preferably is the area of the navel. When the concentration of the protein of the present invention in body fluids, tissues or cells of the control-animals or in prepared solutions from the body fluids, tissues or cells of the control-animal are plotted on the X-axis and the amounts of intraabdominal adipose tissue, e.g. the area of intraabdominal adipose tissue in a section of the abdomen, are plotted on the Y-axis, there appears a direct relationship or positive correlation between the concentrations of the protein of the present invention in the control solutions and the amounts of intraabdominal adipose tissue. The plurality of plots thus obtained are statistically processed whereby the concentration of the protein of the present invention in the control solution and the amount of intraabdominal adipose tissue are expressed as variables which are different from each other. In this regard, the correlation therebetween, for example, may use the linear function such as the correlation $Y=aX+b$. The reliability (i.e., coefficient of correlation) of this correlation is improved as the number of plots is increased. The number of plots may be, more specifically, e.g. 50 to 500 or so, and by way of an example, a coefficient of correlation such as about 0.7 may be obtained from about 100 plots.

To determine the amount of intraabdominal adipose tissue in the test-animal, the concentration of the protein of the present invention in body fluids, tissues or cells of said test-animal or in or in a prepared test solution from the body fluids, tissues or cells of the test-animal is determined by e.g. a method described below. The concentration thus determined is substituted for X in the above obtained correlation, e.g. the correlation $Y=aX+b$, whereby Y may be calculated as the amount of intraabdominal adipose tissue in said test-animal.

Hereinafter, the examination method of the present invention is further described. It has been revealed that excessive accumulation of intraabdominal adipose tissue is related closely to the onset of diseases including metabolic disorders such as diabetes, hyperlipemia and arteriosclerosis as well as cardiac vessel disorders such as coronary artery diseases, angina and myocardial infarction (Visceral Fat-Type Obesity, 1995, published by Iyaku Journal Ltd.). Further, since the concentration of the protein of the present invention in a control solution is in a positive relationship with the amount of intraabdominal adipose tissue as described above, the concentration of the protein of the present invention in a control solution is related closely to the onset of said diseases. Accordingly, (1) the increase or decrease of the amount of intraabdominal adipose tissue in the same test-animal for a predetermined period is examined by use of the analytical method of the present invention, (2) the increase or decrease of the concentration of the protein of the present invention in a body fluid, tissue or cell of the same test-animal or in a prepared test solution from the body fluid, tissue or cell of the test-animal for a predetermined period is examined, (3) the amount of intraabdominal adipose tissue in a test-animal is determined by use of the analytical method of the present invention and then compared with the amount of intraabdominal adipose tissue in a healthy animal of the same species of said test-animal or (4) the concentration of the protein of the present invention in a body fluid, tissue or cell of a test-animal or in a prepared test solution from the body fluid, tissue or cell of said test-animal is compared with the concentration of the protein of the present invention in a body fluid, tissue or cell of a healthy animal of the same species of said test-animal or a prepared test solution from the body fluid, tissue or cell of said healthy animal, whereby the risk of onset of the diseases related closely to the increase of the amount of intraabdominal adipose tissue or judging the recovery of a disease in the test-animal can be predicted.

For example, the amount of intraabdominal adipose tissue in a test-animal is determined as a previous amount by the analytical method of the present invention. After a predetermined period, for example, after a period of 0.5 month or more, the amount of intraabdominal adipose tissue in the same test-animal is determined and compared with the previous amount thereof, so that the increase or decrease of the amount of intraabdominal adipose tissue in the same test-animal may be known. Further, by having the amount of intraabdominal adipose tissue in the same test-animal recorded several times, for example, 3 or more times, the change with time of the amount of intraabdominal adipose tissue in the same test-animal may also be known. The risk of onset of the diseases related closely to the increase of the amount of intraabdominal adipose tissue may thereby be predicted. That is, if the amount of intraabdominal adipose tissue in the test-animal is increased, the risk of onset of the diseases is predicted to be higher, whereas if the amount of intraabdominal adipose tissue in the test-animal is decreased, the risk of onset of the diseases is predicted to be lower. Of course, the concentration of the protein of the present invention in body fluids, tissues or cells of the test-animal or in prepared test solutions from the body fluids, tissues or cells of said test-animal may be directly used, in place of the amount of intraabdominal adipose tissue of the test-animal.

The amount of intraabdominal adipose tissue in a test-animal, as determined by use of the analytical method of the present invention, may also be expressed in terms of the area of intraabdominal adipose tissue in a section of the abdomen. As such, the risk of onset of the diseases is predicted to be high when said area is higher than a standard area regarded as being indicative of a high risk of onset of the diseases. In addition, the risk of onset of the diseases is predicted to be low when said area is lower than the standard area regarded as being indicative of a high risk of onset of the diseases. The standard area regarded as being indicative of a high risk of onset of the diseases is varied depending on the species, sex and age of a test-animal and the type of disease etc., but the preferred standard area for humans is e.g. about 90 to 130 $cm^2$.

The amount of intraabdominal adipose tissue in a test-animal or the concentration of the protein of the present invention in body fluids, tissues or cells of the test-animal or a prepared solution from the body fluids, tissues or cells of said test-animal, as determined by use of the analytical method of the present invention, may also be compared with an average amount of intraabdominal adipose tissue or an average concentration of the protein of the present invention in test solutions obtained from a population composed mainly of healthy individuals of a similar species of the test-animal, preferably an identical species (or an identical human race when the test-animal is humans), an identical sex and a similar age of the test-animal. If the resulting value of the test-animal is higher than the average values, the risk of onset of the diseases is typically higher. If the value of the test-animal is e.g. twice as high as the average value, the risk of onset of the diseases is predicted to be high, and if the value is about thrice as high as the average value, the risk of onset of the diseases is predicted to be extremely high, although said prediction depends on the type of disease.

The analytical method as described above is very useful for managing the test-animals to maintain their health.

The protein of the present invention may be used in analyzing the amount of intraabdominal adipose tissue in a test-animal, that is, an analysis of the intraabdominal adipose tissue which comprises determining the amount of intraabdominal adipose tissue in the test-animal from the concentration of the protein of the present invention in a body fluid, tissue or cell of the test-animal or in a prepared test solution from the body fluid, tissue or cell of said test-animal, based on the positive relationship between the concentration of the protein of the present invention and the amount of intraabdominal adipose tissue in a control-animal, in order to analyze the amount of intraabdominal adipose tissue in the test-animal.

The test-animal to which the analytical method of the present invention and the examination method of the present invention as described above are applicable includes e.g. mammals, and preferably humans and monkeys.

A method of measuring the concentration of the protein of the present invention in a body fluid, tissue or cell of an animal or in a prepared solution from the body fluid, tissue or cell of said animal, or in a body fluid, tissue or cell of a test-animal or in a prepared test solution from the body fluid, tissue or cell of said test-animal may be any method being capable of specifically identifying said protein, with examples thereof including:

1) an immunochemical analysis using an antibody against a protein encompassed the amino acid sequence shown in SEQ ID NO:1;

2) a method wherein the supernatant, obtained by centrifugation of a control solution or a test solution, is applied to liquid chromatography thereby separating and fractionating proteins contained in the supernatant, and the protein of the present invention is identified and quantified by mass spectroscopy;

3) a method wherein a control solution or a test solution is pretreated for removal of unnecessary proteins such as, albumin and immunoglobulin, and then subjected to two-dimensional electrophoresis, and the components in the control are separated and developed two-dimensionally, based on the difference in the isoelectric points and molecular weights of proteins to identify and quantify a spot of the protein of the present invention (Proteome Research: New Frontiers in Functional Genomics, p. 190, 1997, published by Springer); and 4) a method wherein molecules (DNA, RNA, protein, low-molecular compound etc.) being capable of specifically recognizing the protein of the present invention are selected from a molecular library synthesized at random, and based on the specificity and affinity of the protein of the present invention for said molecules, the protein of the present invention is specifically separated and quantified from a control solution or a test solution.

Among those methods described above, the immunochemical analysis is described below in detail as a more specific example.

(1) Preparation of Antigen

To prepare an antibody used in the immunochemical analysis, an Char antigen is first prepared. As the antigen, a protein encompassed by the amino acid sequence shown in e.g. SEQ ID NO:1 (referred to hereinafter as antigen protein) may be used.

The antigen protein may be produced and obtained in a large amount by conventional genetic engineering techniques (e.g., techniques described by J. Sambrook, E. F. Frisch, T. Maniatis: Molecular Cloning 2n d edition, Cold Spring Harbor Laboratory press) by using a gene coding for the antigen protein, for example, DNA having a nucleotide sequence coding for the amino acid sequence shown in SEQ ID NO:1, more specifically, a DNA encompassed by the nucleotide sequence shown in SEQ ID NO:6. In more detail, a plasmid which is capable of permitting a gene coding for the antigen protein to be expressed in host cells is prepared and transfected into host cells, and the resulting transformant is cultured.

Examples of such host cells may include eukaryote and procaryote microorganisms or animal cells such as mammalian and insect cells, and preferably include E. coli.

The plasmid is one which can autonomously multiply and includes genetic information for being able to replicate in host cells, and preferable plasmids also can be easily isolated and purified from host cells, contain a promoter capable of functioning in host cells and have a gene coding for the antigen protein introduced into an expression vector carrying a detectable marker. A wide variety of expression vectors are commercially available, and for example, expression vectors carrying a promoter such as lac, trp or tac used for expression in *E. coli* are commercially available from e.g. Pharmacia and Takara Shuzo Co., Ltd. Restriction enzymes used for introducing the gene encoding the antigen protein into the expression vector are also commercially available from e.g. Takara Shuzo Co., Ltd. Further, a ribosome-binding region may be ligated to a region upstream from the gene encoding the antigen protein so that higher expression is brought about in some cases. The ribosome-binding region is known according to a report of Guarente, L. et al. (Cell, 20, 543 (1980)) or a report of Taniguchi et al. (Genetics of Industrial Microorganisms, p. 202, (1982) published by Kodansha).

The plasmid thus obtained can be introduced into the host cells by usual genetic engineering techniques.

Culturing of the host cells can be carried out by conventional techniques employed for microbial cultures. For example, the host cells are cultured in a medium containing suitable carbon and nitrogen sources as well as trace nutrients such as vitamins. The method for culturing may perform in either solid or liquid medium, preferably shake culture under aeration.

From the host cells thus obtained, the antigen protein may be prepared by a combination of techniques usually employed in isolation and purification of general proteins. For example, after culturing, the antigen protein may be purified by collecting the host cells in a centrifuge, lysing or conducting bacteriolysis on the host cells, optionally solubilizing the antigen protein and performing a combination of various chromatographic steps such as ion-exchange, hydrophobic and gel filtration chromatography. Operations for refolding the structure of the protein may be further conducted if necessary.

For preparing the antibody used in the immunochemical analysis described above, an antigen prepared by the following methods may also be used. Examples of the methods include a method wherein an antigenic peptide containing a particular partial amino acid sequence of the amino acid sequence of the protein of the present invention is rendered polymeric, or a method wherein the antigenic peptide is bound directly or indirectly with a spacer, to a high-molecular carrier to form a complex. Such methods are typically those wherein the antigenic peptide which due to a low molecular weight, is partially antigenic by itself, that is, an incomplete antigen, and is converted into a complete antigen by increasing its molecular weight. Hereinafter, the process of converting the antigenic peptide into a complete antigen is described.

The antigenic peptide may be selected by using e.g. a method for predicting an epitope in a protein as described in "Experimental Protocols on Anti-Peptide Antibody" published by Shujunsha. Usually, a peptide consisting of 10 to 20 amino acids is selected as the antigenic peptide. The used antigenic peptide containing a particular amino acid sequence used is preferably a peptide of high purity, and its synthesis and purification are also described in the "Experimental Protocols on Anti-Peptide Antibody" published by Shujunsha. For example, the antigenic peptide can be purified beforehand by ordinary techniques such as high performance liquid chromatography, if necessary.

The method of rendering the antigenic peptide polymeric includes e.g. the MAP (multiple antigen peptide) method devised by Tam et al. (Proc. Nati. Acad. Sci. USA, 85, 5409, 1988). According to such a method, a lysine residue is introduced to the C-terminus of the antigenic peptide during the synthesis thereof and the peptide is branched sequentially by using the α- and ε-amino groups of the lysine to render the antigenic peptide polymeric so that the antigenecity of the peptide is increased. Since various kinds of previously branched and lysine-bound resin for MAP are commercially available, each of the amino acids in the antigenic peptide containing a particular partial amino acid sequence of the amino acid sequence of the antigen protein may be sequentially added to such a resin by using conventional peptide synthesis methods to elongate its peptide chain.

In the method wherein the antigenic peptide containing a particular partial amino acid sequence of the amino acid sequence of the antigen protein is bound directly or indirectly with a spacer, to a high-molecular carrier molecule to form a complex, the high-molecular carrier molecule used for binding with the antigenic peptide may have reactive groups freely available for a linking reaction with the antigenic peptide containing a particular amino acid sequence or a compound having a spacer bound thereto (hereinafter referred to collectively as the incomplete antigen), and be capable of conferring immunogenicity thereto or capable of raising the original immunogenicity of the antigenic peptide by being linked to said incomplete antigen. The macromolecular compound containing freely available reactive amino groups is particularly preferable. An example of such macromolecular compounds include lysine-enriched proteins having a molecular weight of about 10,000 to 150,000. More specifically, such macromolecular compounds include bovine serum albumin (BSA: molecular weight 66200), human serum albumin (HSA: molecular weight 58000), rabbit serum albumin (RSA: molecular weight 68000), goat serum albumin (GSA: molecular weight 68000) and keyhole limpet hemocyanin (KLH: molecular weight >1000000). Other macromolecular compounds which can meet the requirements described above may also be used as carrier molecules, and such compounds include e.g. porcine thyroglobulin, B2 microglobulin, hemocyanin, immunoglobulins, toxins (chorea toxin, tetanus toxin, diphtheria toxin etc.), polysaccharides, liposaccharides, natural occurring or synthetic polyadenylic acid and polyuridylic acid, polyalanyl and polylysine polypeptides or cellular membrane components such as formalin- or glutaraldehyde-treated erythrocyte cellular membranes.

The method for binding the incomplete antigen to the high-molecular carrier molecule described above may be a method in which the region of a particular amino acid sequence in the incomplete antigen may remain freely available so that a specific immune response is inducible, that is, which may have the production of a specific antibody inducible. More specifically, for example, it is preferred that (1) an incomplete antigen in which the particular amino acid sequence is located, as much as possible, at the most outermost surface thereof is selected and (2) the site of the particular amino acid sequence in the selected incomplete antigen is located, as much as possible, at the outermost surface from the high-molecular carrier molecule.

If the reactive group in the incomplete antigen is a reactive amino group, a reactive group of a spacer is bound to one of the reactive amino groups in the high-molecular carrier molecule by use of e.g. a dialdehyde such as glutaraldehyde. If the reactive group in the incomplete antigen is a reactive SH group, the reactive group in the incomplete antigen is bound by using e.g. oxidative reaction, to one of the reactive SH groups in the high-molecular carrier molecule. If the reactive group in the incomplete antigen is one of the reactive carboxyl group, the reactive group in the incomplete antigen is bound to one of reactive amino groups in the high-molecular carrier molecule by use of e.g. carbodiimide, preferably 1-ethyl-3-(3-dimethylaminopropyl)carbodiimide hydrochloride. By way of an example, an incomplete antigen having a reactive carboxyl group may be bound to a reactive amino group in the high-molecular carrier molecule by e.g. an active ester method described by H. Hosoda et al. in Chem. Pharm. Bull. 31 (11), 4001–4007 (1983) or by a mixed acid anhydride method described by B. F. Erlanger et al. in J. Biol. Chem., 234. 1090–1094 (1959).

The spacer used for when indirectly linking with the spacer is a compound containing one or more kinds of reactive groups capable of forming a covalent bond with a freely available reactive group in the high-molecular carrier molecule. An example of the spacer is a compound containing 2 to 16 cross-linking carbon atoms and having one or more reactive groups such as an amino group, carboxyl group, maleimide group or SH group. More specifically, a compound of the general formula $H_2N(CH_2)_nCOOH$ (n is an integer of 2 to 16) is a preferable example. Linking of the spacer to the antigenic peptide containing a particular amino acid sequence may be conducted in a similar manner as the above-described method for binding a reactive group in the incomplete antigen to one of the reactive groups in the high-molecular carrier molecule.

(2) Step of Immunization and Sensitization of Mammals and Acquisition of an Antibody The antigen thus obtained is used to immunize mammals such as mice, hamsters, guinea pigs, chickens, rats, rabbits and dogs according to the usual immunization and sensitization methods described by e.g. W. H. Newsome et al. in J. Assoc. Off. Anal. Chem. 70(6), 1025–1027 (1987). The antigen may be administered once or several times.

The antigen is administered preferably 3 or 4 times at 7- to 30-day intervals, particularly 12- to 16-day intervals. The dose thereof is, for example, approximately 0.05 to 2 mg of the antigen for each administration. The administration route may be selected from subcutaneous administration, intracutaneous administration, intraabdominal administration, intravenous administration and intramuscular administration, and an injection given intravenously, intraabdominally or subcutaneously is a preferable administration form. In addition, a combination of the subcutaneous injection and the intraabdominal injection is particularly preferable. In such cases, the antigen is usually used after being dissolved in a suitable buffer, for example, sodium phosphate buffer or physiological saline containing a kind of ordinarily used adjuvant such as complete Freund's adjuvant (a mixture of Aracel A, Bayol F and dead tubercule bacillus), RAS [MPL (monophosphoryl lipid A)+TDM (synthetic trehalose dicorynomycolate)+CWS (cell wall skeleton) adjuvant system] or aluminum hydroxide. However, depending on the administration route or conditions, the adjuvants described above may not be used. As used herein, the "adjuvant" means a substance which upon administration with the antigen, enhances a immune reaction unspecifically against the antigen.

After the mammal is left for 0.5 to 4 months without an administration thereof, a small amount of blood is sampled from e.g. an ear vein of the mammal and measured for antibody titer. When the antibody titer is increasing, administration of the antigen is conducted repeatedly an appropriate number of times, depending on cases. For example, the antigen may be administered 1 to 5 times at a dose of 100 $\mu g$ to 1 $\mu g$ for each administration. One to two months after the final administration, blood is collected in a usual manner from the immunized and sensitized mammal, and by having the blood separated and purified by conventional techniques such as precipitation by centrifugation or with ammonium sulfate or polyethylene glycol and chromatography such as gel filtration chromatography, ion-exchange chromatography and affinity chromatography, the antibody used in the present invention may be obtained as a polyclonal antiserum. Further, the antiserum may be subjected to treatment e.g. at 56° C. for 30 minutes to inactivate the complement system.

Further, immunocompetent B cells are isolated from the immunized and sensitized mammal described above, and the immunocompetent cells are fused with tumor cells capable of continuous cell division, and the formed fusion cells are then isolated. After screening, hybridoma cells producing the desired antibody are cloned, and the hybridoma cells are cultured in vitro or in vivo to produce the monoclonal antibody, whereby an antibody having high degrees of specificity and affinity may also be produced.

(3) Quantification of the Protein of the Present Invention by the Antibody

The method of measuring the concentration of the protein of the present invention by the antibody thus prepared is described by reference with the following typical examples.

In accordance with the present invention, as an antibody used in the following techniques for quantifying the protein of the present invention, there may be used molecules containing antibody activity such as a polyclonal or monoclonal antibody, any class and subclass of an antibody, as well as a Fab and Fab' fragment.

(A) Immunoblotting Techniques

In immunoblotting techniques, the protein of the present invention bound to a solid carrier is recognized by an antibody against said protein (hereinafter, said antibody is referred to as primary antibody) and the antibody is detected. The principles and outline of such a method are described in e.g. Antibodies—A Laboratory Manual, p. 471 (1988, Cold Spring Harbor Laboratory).

As the solid carriers, nitrocellulose formed in the shape of a membrane, sheet, filter etc. is generally used, but the solid carriers are not particularly limited insofar that the protein of the present invention may adhere well thereto and the solid carriers do not eliminate the antigenecity of the protein of the present invention. If a nitrocellulose membrane is used, a solution obtained by diluting the protein of the present invention at a suitable concentration with a suitable buffer such as phosphate buffered saline is spotted onto the nitrocellulose membrane, whereby the protein of the present invention is bound to the nitrocellulose membrane. The amount of the spot for quantification thereof is preferably about 1 $\mu l/3$ $mm^2$ or an amount in which the primary antibody is in excess. To permit the protein of the present invention to be recognized by the primary antibody, it is preferable to treat a sample containing the protein of the present invention with e.g. 0.1% (w/v) SDS or have 0.1% (w/v) of SDS in the buffer used when binding to nitrocellulose membrane. Alternatively, a sample containing the protein of the present invention is diluted with a suitable buffer such as phosphate buffered saline and electrophoresed in acrylamide gel of suitable concentration. The protein of the present invention after electrophoresis is transferred onto a suitable membrane such as Hybond-N (Amersham) by electroblotting techniques or semi-dry techniques (Bio Experiment Illustrated 5, p. 105, published by Shujyunsha).

To prevent the antibody from adhering nonspecifically to sites not containing the protein of the present invention on the nitrocellulose membrane with the protein of the present invention thus spotted or on the nitrocellulose membrane to which the protein of the present invention was transferred by electrophoresis, the nitrocellulose membrane to which the protein of the present invention has been bound is incubated for about 20 minutes to 24 hours at room temperature to 37° C. with a solution containing high-molecular carrier molecules not recognized by the primary antibody, that is, gelatin, skimmed milk or high-molecular carrier molecules (e.g. serum albumin from a different kind of animal such as goat, cattle) which among the high-molecular carrier molecules usable in the step of converting the antigenic peptide containing a particular amino acid sequence into a complete antigen, are not used in production of the primary antibody, so that the surface of the nitrocellulose membrane is covered with the high-molecular carrier molecules. After incubation, the nitrocellulose membrane is washed to remove the above high-molecular carrier molecules in a free state. The nitrocellulose membrane thus prepared is mixed with a prepared solution containing the primary antibody and then incubated for about 10 minutes to 3 hours at room temperature to 37° C. under stirring. The prepared solution containing the primary antibody refers to a prepared solution in which the primary antibody can be present in a free form in distilled water or a solution such as a buffer and saline. In this manner, the protein of the present invention is recognized by the primary antibody. Hereinafter, the method of detecting the antibody is described.

If the primary antibody has been labeled with an enzyme such as peroxidase, alkaline phosphatase, β-D-galactosidase, glucose oxidase, glucoamylase, carboxylic anhydrase, acetylcholine esterase, lysozyme, malate dehydrogenase and glucose-6-phosphate dehydrogenase, the primary antibody in a free form is removed by washing after incubation, a substrate for the above labeled enzyme is allowed to act on the enzyme and the reaction is measured by use of coloration so that the primary antibody may be detected. For example, if the primary antibody is labeled with a peroxidase, a combination of hydrogen peroxide as the substrate and diaminobenzidine or o-phenylene diamine as the coloring reagent yields brown or yellow coloration, and thus the concentration of the protein of the present invention can be determined by quantifying the absorption at a wavelength corresponding to said coloration. For an alternative method of detecting a peroxidase-labeled antibody-antigen complex, an ECL detection system (Clin. Chem. vol. 25, p. 1531, 1979) (Amersham) by which a signal from the target antigen may be detected on an X-ray film by chemiluminescence is commercially available. In such a method, the signal detected on the X-ray film can be quantified with a densitometer. In the case of the primary antibody labeled with glucose oxidase, e.g. 2,2'-acido-di-(3-ethylbenzothiazoline-6-sulfonic acid (ABTS) is used. In the case in which the primary antibody is labeled with biotin, streptoavidin having affinity for biotin may be used to detect a signal from the antigen by a similar coloration reaction to that of the primary antibody labeled with an enzyme.

Further, when an enzyme-labeled secondary antibody recognizing and binding to the primary antibody is used, the primary antibody in a free form is removed by washing after incubation, and then the membrane is incubated with the secondary antibody. Said secondary antibody labeled with an enzyme, for example, is an antibody against the primary antibody and is labeled with an enzyme such as peroxidase, alkaline phosphatase, β-D-galactosidase, glucose oxidase, glucoamylase, carboxylic anhydrase, acetylcholine esterase, lysozyme, malate dehydrogenase and glucose-6-phosphate dehydrogenase, or is an antibody against the primary antibody and is labeled with biotin. More specifically, when a rabbit anti-serum is used as the primary antibody, the secondary antibody is preferably e.g. peroxidase-labeled anti-rabbit immunoglobuhn (IgG) donkey immunoglobulin (IgG) or anti-rabbit immunoglobulin (IgG) goat immunoglobulin (IgG). The anti-rabbit IgG donkey IgG or the anti-rabbit IgG goat IgG is on the market and easily available. As the method of detecting these secondary antibodies, there may be mentioned a similar method of detecting the labeled primary antibody as described above. Further, $^{125}$I labeled-protein A [Amersham] may also be used as the secondary antibody. This method makes use of the ability of protein A to bind to the antibody, so that the signal may be detected on an X-ray film and quantified by a densitometer.

(B) Separation by Immunoprecipitation

In a method of immunoprecipitation, the protein of the present invention is recognized by the primary antibody, the resulting immune complex containing the antibody and the protein of the present invention is purified to separate the protein of the present invention, and techniques such as gel electrophoresis, enzyme activity measurement and immunoblotting techniques are utilized for quantification of the protein of the present invention.

First, a sample containing the protein of the present invention is mixed with the primary antibody against the protein of the present invention for e.g. about 1 to 24 hours at 4° C. under stirring whereby an immune complex thereof is formed. The mixing ratio of the sample to the primary antibody is e.g. about 1:8, which shall however vary, depending on the amount of the protein of the present invention. Preferably, the sample is previously treated with 0.1% (w/v) SDS.

Then, a secondary reagent which is capable of binding specifically to the primary antibody and separating the primary antibody and the protein of the present invention bound specifically to the primary antibody from the solution is added if necessary to the formed immune complex, and the resulting mixture is incubated whereby a complex containing the immune complex and the secondary reagent is formed and then recovered. The secondary reagent includes, for example, antibody-binding proteins located on bacterial cell walls, such as protein A and protein G, or anti-immunoglobulin antibodies. If a secondary reagent previously bound to insoluble carriers is used, the complex containing the immune complex and the secondary reagent may be recovered very easily by centrifugation and washing. Alternatively, without substantially using the secondary reagent, a primary antibody bound directly to insoluble carriers may be added to a sample solution containing the protein of the present invention, and the protein of the present invention thus rendered insoluble may be recovered. The insoluble carriers may have a very wide variety of designs and shapes depending on the specifically intended purposes of use. For example, beads, dishes, spheres, plates, small rods, cells, small bottles, small tubes, fibers and nets may be mentioned as the insoluble carrier. More specific examples include beads (e.g., Sepharose, Bio-Gel etc.) made of polysaccharides such as agarose and microtiter plates made of transparent plastic materials such as polyvinyl chloride or polystyrene, as well as small spheres, tubes or rods made of polystyrene and polystyrene latex. For example, agarose-based beads such as cyanogen bromide-activated Sepharose and Affi-Gel, cellulose-based beads and polyacrylamide-based beads are commercially available, and functional groups on the beads thereof have previously been activated so that the secondary reagent or the primary antibody may be bound thereto directly by a coupling reaction (Affinity Chromatography, published by Pharmacia, or Nature, vol. 214, p. 1302, 1967). Further, protein A and protein G bound previously to agarose-based beads are also commercially available.

Subsequently, the protein of the present invention is released from the recovered complex by procedures such as heat treatment or elution with a low-pH buffer. Then, the protein of the present invention in a free form can be detected and quantified by techniques such as gel electrophoresis, enzyme activity measurement and immunoblotting techniques.

(C) Enzyme Immunoassays

Enzyme immunoassays include e.g. a sandwich method and competitive assay. In the sandwich method, a sample containing the protein of the present invention is allowed to react with the primary antibody bound to solid carriers, free components not bound to the solid carriers are removed by washing and the amount of the protein of the present invention which has formed an antigen-antibody complex on the solid carriers is quantified with a labeled secondary antibody or a labeled antibody specifically binding to the secondary antibody, whereby the concentration of the protein of the present invention in the sample is determined.

In the competitive assay, an antigen or a primary antibody bound to solid carriers are reacted such that the antigen is reacted competitively with a sample containing the protein of the present invention and the primary antibody and the primary antibody is reacted competitively with the sample containing the protein of the present invention and the free competitive antigen. Thereafter, free components not bound to the solid carriers are removed by washing. The amount of the antibody or competitive antigen which has formed an antigen-antibody complex on the solid carriers is quantified through the enzyme molecule labeled with said antibody or antigen or through the labeled secondary antibody specifically binding to the primary antibody, whereby the concentration of the protein of the present invention in the sample is determined.

The principles and detailed procedures of such techniques are described in "Seikagaku Jikkenho 11 (Biochemical Experimental Method 11) (Tokyo Kagaku Dojin Ltd.) and Method in Enzymology, vol. 70 (Academic Press).

The sandwich assay is further described by reference with the following typical example.

The primary antibody may be bound directly to solid carriers or indirectly thereto with a spacer or a high-molecular carrier molecule not recognized by the secondary antibody and the labeled antibody specific to the secondary antibody. As used herein, the "high-molecular carrier molecule not recognized by the secondary antibody and the labeled antibody specific to the secondary antibody" refers to a high-molecular carrier molecule which among the high-molecular carrier molecules usable in the step of converting the antigenic peptide containing a particular amino acid sequence of the antigen to a complete antigen, is not used in production of the secondary antibody and the labeled antibody specific to the secondary antibody. Further, in cases wherein the primary antibody is to be bound with a spacer or a high-molecular carrier not recognized by the secondary antibody and the labeled antibody specific to the secondary antibody, the spacer of high-molecular carrier may be bound in a similar manner to that described in the step of converting the antigenic peptide containing the particular amino acid sequence to a complete antigen.

The solid carriers used for direct or indirect binding of the primary antibody include ordinarily used materials such as polystyrene, polyacryl, polycarbonate, polymethacrylate, Teflon™, nitrocellulose membrane, filter paper, dextran, glass, agarose, ferrite and latex (natural rubber). The solid carriers may assume a very wide variety of designs and shapes depending on specifically intended purposes of use. For example, dishes, spheres, plates, small rods, cells, small bottles, small tubes, fibers, nets, gels and column resins may be mentioned as designs thereof. By way of more specific examples, microtiter plates made of transparent plastic materials such as polyvinyl chloride or polystyrene, small spheres, tubes or rods made of polystyrene and polystyrene latex can be mentioned as the solid carrier.

For binding the primary antibody to the solid carriers directly or indirectly with a spacer or a high-molecular carrier molecule not recognized by the secondary antibody and the labeled antibody specific to the secondary antibody (referred to hereinafter as coating), a non-covalent and covalent method can be applied.

For covalent binding, the solid carriers are, for example, previously activated in a conventional manner with glutaraldehyde or cyanogen bromide.

The coating solution used therein includes e.g. about 10 mM phosphate buffer (pH 7.4) containing 140 mM sodium chloride, or PBS (140 mM NaCl, 2.7 mM KCl, 10 mM $Na_2HPO_4$, 1.8 mM $KH_2PO4$ (pH 7.4)). Preferable coating conditions are that the concentration of the primary antibody in the coating solution is preferably e.g. about 0.05 $\mu$g/ml to 100 $\mu$g/ml and the coating time is from several hours to several days, and preferably e.g. about 6 hours to 24 hours. The coating temperature thereof is e.g. 4 to 37° C. To avoid non-specific binding, a solution containing 0.1~5% bovine serum albumin, gelatin or skim milk is added to the thus obtained primary antibody bound directly or indirectly to the solid carrier before a sample containing the protein of the present invention is added to the thus obtained primary antibody bound directly or indirectly to the solid carrier.

A sample containing the protein of the present invention is added to the thus obtained primary antibody bound directly or indirectly to the solid carrier and then incubated at 4 to 37° C. After being incubated for about several minutes to several days, preferably 2 hours to overnight, the solid carrier is washed. Then, a solution containing the secondary antibody is added thereto and incubated at 4 to 37° C. for about 10 minutes to overnight. If the secondary antibody has been labeled with biotin or an enzyme such as peroxidase, alkaline phosphatase, β-D-galactosidase, glucose oxidase, glucoamylase, carboxylic anhydrase, acetylcholine esterase, lysozyme, malate dehydrogenase or glucose-6-phosphate dehydrogenase, then the amount of the secondary antibody bound to the solid carrier may be directly measured by the method described above in the immunoblotting techniques.

If an enzyme- or biotin-labeled antibody which can recognize the secondary antibody and specifically bind thereto is used, then the free secondary antibody is removed by washing, and the solid carrier is incubated with a solution of said labeled antibody at 4 to 37° C. After incubation of about 10 minutes to overnight, the solid carrier is washed and the amount of the labeled antibody bound to the solid carrier after washing is determined. Said labeled antibody includes an antibody labeled with e.g. biotin or an enzyme such as peroxidase, alkaline phosphatase, β-D-galactosidase, glucose oxidase, glucoamylase, carboxylic anhydrase, acetylcholine esterase, lysozyme, malate dehydrogenase or glucose-6-phosphate dehydrogenase.

In cases of using the labeled antibody specific to the secondary antibody, the primary and secondary antibodies are usually of a different class or derived from a different animal species to substantially avoid the binding of labeled antibody specific to the secondary antibody to the primary antibody bound to the solid carrier. For example, when a mouse monoclonal antibody is used as the primary antibody bound to the solid carrier, a rabbit polyclonal antibody can be used as the secondary antibody and a peroxidase-labeled donkey or goat anti-rabbit IgG can be used as the labeled antibody specific to the secondary antibody.

In the method described above, a calibration curve is previously prepared using various diluted solutions containing the protein of the present invention at known concentrations. Then, a sample containing the protein of the present invention at a concentration not known is measured, and the concentration of the protein of the present invention in the sample is determined, based on the calibration curve.

(D) Radioimmunoassays

The basic principles of the radioimmuno assays are substantially the same as in enzyme immunoassays. By way of an example, a sample containing the protein of the present invention is added to a reaction solution containing known amounts of a labeled antigen and an antibody, such that there is a competitive reaction. Then, the produced antigen-antibody complex and the antigen in a free form are separated from each other, and either of them is quantified and compared with a calibration curve whereby the concentration of the protein of the present invention in the sample solution is quantified (New Lecture on Experiments in Biochemical Chemistry 12, published by Tokyo Kagaku Dojin, and Method in Enzymology, vol. 70, published by Academic Press).

Usually, the antigen used in radioimmunoassays are labeled with $^{125}$I, and the introduction of $^{125}$I to the antigenic protein may be conducted according to the method of Bolton-Hunter (Biochem. J., vol. 133, p. 529, 1973) or the chloramine T method.

The measurement is usually conducted by using a gamma counter, and in a similar manner as in enzyme immunoassays, a calibration curve is previously prepared using solutions containing the antigen at known concentrations. Then, a sample containing the protein of the present invention at a concentration not known is measured, and the concentration of the protein of the present invention in the sample may be determined, based on the calibration curve.

Hereinafter, a kit of the present invention is described. The kit for carrying out the analytical method of the present invention and the examination method of the present invention may be prepared. The kit may comprise the protein of the present invention as a standard reagent for analyzing the amount of intraabdominal adipose tissue in an animal, and preferably, the kit when used for carrying out the analytical method of the present invention by using immunochemical analysis also comprises an antibody against the protein of the present invention.

Further, the kit of the present invention may comprise the following constitutional ingredients. That is, the constitutional ingredients which may be contained for the sandwich method in enzyme immunoassays typically include (1) a solid carrier, (2) a reagent containing an antibody against the protein of the present invention, that is, the primary antibody, (3) a reagent containing the secondary antibody and (4) a reagent containing a labeled antibody against the secondary antibody, that is, a reagent containing an antibody which is labeled with an enzyme and which can recognize the secondary antibody and can specifically bind thereto. Additionally, as needed, (5) a substrate compound for the enzyme used in labeling the antibody, (6) a standard reagent containing a protein encompassed by the amino acid sequence shown in SEQ ID NO:1 or a protein which can be recognized by an antibody against said protein, (7) a buffer, (8) additives such as a detergent and high-molecular carriers for preventing non-specific adhering and formation of aggregates and (9) a pipette, a reaction vessel or a calibration curve may also be included therein.

The solid carrier in (1) may have the primary antibody in (2) previously bound thereto directly or indirectly with a spacer or a high-molecular carrier molecule not recognized by the secondary antibody and the labeled antibody specific to the secondary antibody.

The reagent containing the primary antibody in (2), the secondary antibody in (3) or the labeled antibody in (4) may be provided in the form of a solution in a buffer or water, or may be provided as a lyophilized product to be dissolved just before use. Further, (2), (3) and (4) may contain a stabilizer such as bovine serum albumin at a final concentration of about 0.1 to 10% (W/V) when dissolved, and if so desired, a detergent such as Tween 20 may also be contained at a final concentration of 0.1 to 2% (W/V) when dissolved.

The buffer in (7) may be a buffer which may be used to dilute a body fluid, tissue or cell of a control-animal or in a prepared solution from the body fluid, tissue or cell of the control animal or a body fluid, tissue or cell of a test-animal or in a prepared test solution from the body fluid, tissue or cell of the test-animal, as well as which may be used to wash the solid carriers and to dissolve and dilute the ingredients in (2), (3), (4) and (5) above.

Further, the analytical method of the present invention and the examination method of the present invention may also be conducted by use of a combination of devices. By way of an example, in the analytical method of the present invention and the examination method of the present invention using immunochemical analysis for measurement of the concentration of the protein of the present invention, there are used devices produced to include (1) a thermostatic chamber for incubating a body fluid, tissue or cell of a control-animal or a prepared solution from the body fluid, tissue or cell of said control-animal or a body fluid, tissue or cell of a test-animal or in a prepared solution from the body fluid, tissue or cell of said test-animal, together with the antibody-containing reagent, at a temperature in which the protein of the present invention in the control solution or in the test solution can react with the antibody, (2) a detector selected from a densitometer for detecting a signal in immunoblotting techniques or immunoprecipitation, a photometer for measuring the absorbance or fluorescence of a reaction solution in enzyme immunoassays and a γ-counter used in radioimmunoassays, (3) computer software for calculating the amount of intraabdominal adipose tissue in a test-animal from the measurement of the concentration of the protein of the present invention in the test solution obtained in (2), based on the positive relationship between the concentration of the protein of the present invention in the control solution and the amount of intraabdominal adipose tissue, and (4) a computer for executing calculation in (3).

EXAMPLES

Hereinafter, the present invention is described in more detail by reference to the Examples, which however are not intended to limit the present invention.

Example 1

Isolation of a Gene Coding for a Protein Encompassed by the Amino Acid Sequence Shown in SEQ ID NO:1

1.0 μg of whole RNA prepared from human intraabdominal adipose tissue by the guanidine thiocyanate (GTC)/ cesium chloride (CsCl) method (Chirgwin, J. M. et al., Biochemistry, 18, 5294, 1979) was used as a template and was mixed with oligo dT primers included in a cDNA synthesis kit (Takara Shuzo Co., Ltd.). 50 U of MMTV reverse transcriptase was added thereto in the presence of 1 mM dNTP, and then the mixture was incubated at room temperature for 10 minutes, and then at 42° C. for 15 minutes and at 99° C. for 5 minutes whereby single-stranded cDNA was synthesized.

Then, 55 cycles of PCR, each of the cycles including an incubation at 94° C. for 1 minute, 55° C. for 1 minute and 72° C. for 2 minutes, were conducted in which 2.0 ng of said single-stranded cDNA were used as a template and 20 pmol of each of the oligonucleotides encompassed by the nucleotide sequences shown in SEQ ID NO: 2 or 3 were used as primers in the presence of 200 µM dNTP, 1.5 mM $MgCl_2$ and 1 U of DNA polymerase (Perkin Elmer). The resulting PCR reaction product was subjected to 1% agarose gel electrophoresis (electrophoresis buffer; Tris-boric acid buffer (Nakalai Tesque), and an about 1.5 kbp DNA band was recovered from the gel and cloned into a HincII site in plasmid vector pUC118 (Takara Shuzo Co., Ltd.) by the method described by J. Sambrook, E. F. Fritsch and T. "Maniatis in "Molecular Cloning Second Edition", Cold Spring Harbor Laboratory Press (1989). The DNA thus cloned was sequenced with a 373A DNA Sequencer manufactured by Applied Biosystems, in which Taq Dye Primer Cycle Sequencing Kit and Taq Dye Deoxy Terminator Cycle Sequencing Kit (Applied Biosystems) were also used. The DNA comprised the nucleotide sequence shown in SEQ ID NO:6, and said nucleotide sequence coded the amino acid sequence shown in SEQ ID NO:1.

Example 2

Preparation of Protein Standard (I) Encompassing a Partial Sequence of the Amino Acid Sequence Shown in SEQ ID NO:1

30 Cycles of PCR, each of the cycles including an incubation at 94° C. for 1 minute, 60° C. for 1 minute and 72° C. for 2 minutes were conducted, wherein the DNA cloned in Example 1 was used as a template and oligonucleotides encompassed by the nucleotide sequences shown in SEQ ID NO: 4 or 5 were used as primers. As such, a DNA consisting of a nucleotide sequence between the 96- and 1493-positions in the nucleotide sequence shown in SEQ ID NO:6 was amplified. The amplified DNA was digested with NdeI and BamHI and subcloned to the NdeI and BamHI sites in expression vector pET11a (Novagen) to give expression plasmid pET11a085 (FIG. 1) for expressing a protein having Met added to the amino-terminus of an amino acid sequence starting at amino acid 27 in the amino acid sequence shown in SEQ ID NO:1.

Then, the expression plasmid pET11a085 was transformed into *E. coli* DE3 (Novagen).

The resulting transformant was cultured at 37° C. until the O.D. 600 of the culture reached 0.6, and IPTG was added as an inducer to a final concentration of 1 mM, and the transformant was further cultured overnight. Then, the transformant was harvested by centrifugation, then suspended in 100 mM Tris-HCl buffer (pH 7.6) containing 5 mM EDTA.2Na, 5 mM DTT and 1 mM PMSF (referred to hereinafter as buffer A) and disrupted by sonication (5 minutes×3 times, under cooling on ice), and this disrupted solution was centrifuged at 12,000×g for 15 minutes at 4° C. whereby the precipitate was recovered as an inclusion body fraction.

The inclusion body fraction was suspended in buffer A to which urea had been added to a final concentration of 2 M, followed by sonication (5 minutes, under cooling on ice). The resulting suspension was centrifuged at 12,000×g for 15 minutes at 4° C., and buffer A to which urea had been added to a final concentration of 4 M was added to the resulting precipitate, and the procedure described above was repeated. Further, a similar procedure was repeated using buffer A to which urea had been added to a final concentration of 6 M, and the resulting precipitate was suspended in 20 mM Tris-HCl buffer (pH 8.5) containing 2 mM DTT and 8 M urea and were then centrifuged at 2,000×g for 15 minutes at 4° C., and the supernatant was recovered. The resulting supernatant was subjected to gel filtration chromatography on Hi Load Superdex 200 pg (column, φ16 mm×60 cm (Pharmacia); flow rate, 1.0 ml/min.; detection, 280 nm). A peak fraction eluted at a retention time of from 45 to 55 minutes was collected and concentrated with Centricon™ (fractionation molecular weight of 30,000, a product of Grace Japan (formerly Amicon Ltd.)) and then subjected to Mono Q HR10/10 ion-exchange chromatography (column, φ10 mm×10 cm (Pharmacia); flow rate, 1.0 ml/min.; 1 M NaCl gradient; detection, 280 nm). A fraction eluted with 100 to about 200 mM NaCl was collected and concentrated to 1 mg/ml protein with Centricon™ (fractionation molecular weight of 30,000, a product of Grace Japan). The fraction obtained in the procedure described above were analyzed by SDS-polyacrylamide gel electrophoresis and subsequent silver staining. As a result, a single band was detected.

100 mM Tris-HCl (pH 8.5) was added to the thus obtained fraction under gentle stirring until the final concentration of urea therein was reduced to 6 M. Gentle stirring was further continued at room temperature overnight. Then, said fraction was centrifuged at 18,000×g for 20 minutes at 4° C., the supernatant was then recovered, and 20 mM Tris-HCl buffer (pH 8.5) containing 2 M urea, 4 mM reduced glutathione and 0.4 mM oxidized glutathione was added thereto until the final concentration of urea therein was reduced to 2.5 M. This solution was introduced into a dialysis tube with a cut-off molecular weight of 25,000 and dialyzed at 4° C. for about 8 hours against a 1000-fold excess volume of 20 mM Tris-HCl buffer (pH 8.5) containing 2 mM urea, 4 mM reduced glutathione and 0.4 mM oxidized glutathione. The dialyzate was further dialyzed at 4° C. overnight against a 1000-fold excess volume of 20 mM Tris-HCl buffer (pH 8.5) containing 2 mM reduced glutathione and 0.2 mM oxidized glutathione and then dialyzed at 4° C. overnight against a 1000-fold excess volume of 20 mM Tris-HCl buffer (pH 8.5). An aliquot of the fraction obtained in the procedure described above was analyzed by reverse phase chromatography, and as a result, a single peak was detected, The resulting protein was designated protein standard (I).

Example 3

Preparation of an Antibody Against a Protein Standard (I) (Encompassed by the Amino Acid Sequence Shown in SEQ ID NO:1)

The protein standard (I) prepared in the method of Example 2 was used as an antigen to immunize rabbits, and an antibody was obtained from the animals.

In the first immunization, 1.0 mg of the protein standard prepared in the method described above was mixed with Freund's adjuvant and administered subcutaneously into each rabbit. Thereafter, the antigen was administered, respectively, 4 times at 2 week intervals in a similar manner. One week after the final administration of the antigen, a small amount of serum was obtained from an ear vein of each of the rabbits and measured for antibody titer. Thereafter, the antigen was additionally administered once and blood was collected from each of the rabbits. The blood was centrifuged to give a serum fraction which was then dialyzed overnight against a 100-fold excess volume of 50 mM sodium phosphate buffer (pH 7.0) at 4° C. The dialyzed serum was subjected to protein A (Pharmacia) column chromatography, and the adsorbed fraction was eluted with 100 mM citrate buffer (pH 4.0), and immediately the eluate was neutralized with 1 M Tris-HCl (pH 9.0), so that an antibody solution was obtained.

Example 4

Immobilization of the Antibody Onto Carriers

The antibody obtained in the method of Example 3 was bound to activated cyanogen bromide-Sepharose beads according to a method described in Affinity Chromatography (published by Pharmacia). Specific procedures., are as follows: The antibody was diluted with a buffer comprising 150 mM NaHCO$_3$ and 500 mM NaCl (pH 8.3) (referred to hereinafter as buffer B) to amount to 2.5 mg protein/ml, then applied to a PD-10 column (Pharmacia) and eluted with buffer B. 0.5 g of activated cyanogen bromide-Sepharose beads (Pharmacia) were swollen with 1 mM HCl previously cooled on ice and then gelled by equilibrating the beads with 200 ml of buffer B containing 1 mM HCl. Then, 1.75 ml of the above eluate was added to and mixed with the gel, and the suspension was stirred at 4° C. overnight. This mixed suspension was filtered on a Buchner funnel in which the filtrate was removed under suction. The remaining beads were suspended in 3.0 ml of 1 M ethanolamine containing 500 mM NaCl (pH 8.3) and stirred at 4 0C. for 6 hours to block the remaining active groups. Then, the beads were washed with 3.0 ml of buffer B with suction on a Buchner funnel and then with 3.0 ml of a buffer containing 100 mM acetic acid and 500 mM NaCl (pH 4.0) (referred to hereinafter as buffer C). The operation of alternatingly washing with buffer B and then with buffer C. was repeated 5 times, and the beads were washed several times with a lysis buffer (50 mM Tris-HCl (pH 7.6), 150 mM NaCl, 1% NP-40, 0.02% Na$_3$N), suspended in the lysis buffer at a 1:1 ratio of the gel slurry to the buffer and then stored at 4° C. The antibody in the filtrate after immobilization was not detected by quantification, confirming that the antibody was completely immobilized onto the beads.

Example 5

Measurement of the Concentration of the Protein of the Present Invention in a Sample Solution By Immunoprecipitation and Western Blotting Techniques Serum fractions were prepared from human blood samples by centrifugation (3,000×g, 10 min., 4° C.) and were then used as test solutions. 5 µl of the antibody-immobilized beads prepared in Example 4 were added to 200 µl of the test solutions, respectively, and were gently stirred at 4° C. for 4 hours. The beads were precipitated by centrifugation at 12,000×g for 5 seconds at 4° C. to remove the supernatant, and 500 µl lysis buffer was added, respectively, to the beads which were then gently stirred and then centrifuged at 12,000×g for 5 seconds at 4° C. to remove the supernatant. The procedure above of washing the beads was repeated 4 times, and then 500 µl distilled water was added, repectively, to the beads, and a similar washing procedure as above was repeated 3 times. After centrifugation, the beads were essentially deprived of liquid, and 75 µl of 2% aqueous acetic acid was added, respectively, to the beads which were then gently stirred. The beads were precipitated by centrifugation at 12,000×g for 5 seconds at 4° C., and the supernatant was recovered, and the same extraction procedure was conducted by adding 2% acetic acid again to the beads. The resulting eluates having 2% acetic acid were collected, and bovine serum albumin protein was added to said eluates as a carrier and to a final concentration of 150 µg/ml. Subsequently, 75 µl of a TCA solution was further added, respectively, thereto and the mixtures were left on ice overnight. Such samples were centrifuged at 15,000×g for 20 minutes at 4° C., and the precipitated protein was recovered, washed with 500 µl ice-cold acetone, respectively, and dried.

Figure 2:
FIG. 2 shows the results of detection of a protein of the present invention in blood by immunoprecipitation and Western blotting techniques. In the drawing, the upper arrow indicates the starting point of electrophoresis and the lower arrow indicates the end of electrophoresis. The signal of the immunoprecipitated protein was quantified by a densitometer. Lane 1, 0 ng of antigen protein; lane 2, 0.2 ng of antigen protein; lane 3, 0.5 ng of antigen protein; lane 4, 1.0 ng of antigen protein; lane 5, 2.0 ng of antigen protein; lane 6, blood from examinee 1; and lane 7, blood from examinee 2.
Figure 2:

The resulting precipitates were dissolved in a solution containing 50 mM Tris and 0.04 N aqueous NaOH. After an equal volume of SDS sample buffer was added thereto, the dissolved protein (the protein of the present invention) was subjected to a 10 to 20% SDS-PAGE gel (Bio-Craft Ltd.). The protein in the gel after electrophoresis was transferred onto a Hybond-N membrane (Amersham) by electroblotting techniques (transfer buffer; 25 mM Tris, 192 mM glycine, 20% methanol, 4° C., 80 V, 1.5 hours). The membrane thus prepared was washed with TABS buffer (20 mM Tris-HCl (pH 7.4), 150 mM NaCl, 0.05% Tween 20, 0.05% Na$_3$N) and then incubated in TTBS buffer containing 3% gelatin at 37° C. for 1 hour. Thereafter, the membrane was incubated at 37° C. for 1 hour in a solution containing a 1,000-fold dilution of the antibody obtained in Example 3, TTBS buffer and 1% bovine serum albumin. Then, the membrane was washed 3 times with TTBS buffer at room temperature for 5 minutes and then incubated at 37° C. for 1 hour in a solution prepared by 1000-fold dilution of donkey anti-rabbit IgG antibody labeled with horseradish peroxidase, with TTBS containing 1% bovine serum albumin. Thereafter, the membrane was washed 3 times with TTBS buffer at room temperature for 5 minutes and subjected to ECL detection system (Amersham). The menbrane was exposed to a Hyperfirm ECL film (Amersham), and a fluorescent signal (in the vicinity of 50 Kda) on the Hyperfirm ECL film (Amersham) was detected (FIG. 2).

The intensity of the fluorescent signal thus obtained was quantified with a densitometer. The concentration of the protein of the present invention in each of the test solutions was calculated from the signal intensity of each of the samples, based on a calibration curve previously prepared using 0.1 to 5 ng of the protein standard (a) obtained in Example 2.

Example 6

Measurement of the Concentration of the Protein of the Present Invention in a Test Solution By Enzyme Immunoassays A coating solution was prepared by adding the antibody obtained in Example 3 to PBS (140 mM NaCl, 2.7 mM KCl, 10 mM Na$_2$HPO$_4$ and 1.8 mM KH$_2$PO$_4$ (pH 7.4)) to a concentration of 20 µg/ml therein. The coating solution was put into wells of a 96-well polystyrene microtiter plate at a volume of 150 µl/well and then incubated at 4° C. overnight. After the coating solution was removed, each of the wells was washed twice with 300 µl of PBS, and the microtiter plate was turned upside down and gently tapped against a paper towel to remove the solution in the wells of the plate. Then, PBS containing 1% (W/V) bovine serum albumin was added to the wells of the microtiter plate at a volume of 150 µl/well and incubated at 4° C. overnight for blocking.

After the blocking solution was removed, the microtiter plate was washed twice with 300 µl of a washing solution (50 mM $Na_2PO_4$—$Na_2HPO_4$, 150 mM NaCl, pH 7.4, 2.0% Tween 20). Subsequently, serum fractions were prepared from human blood samples by centrifugation (3,000×g, 10 minutes, 4° C.) and were then used as test solutions. 120 µl of a reaction solution prepared by adding 1% (W/V) bovine serum albumin to the washing solution was added to each of the wells, and then 30 µl of the test solutions were added to each of the wells, repectively, and incubated at room temperature overnight. Then, the reaction solution was removed, and each of the wells was washed 3 times with 300 µl of the washing solution.

Subsequently, an antibody Fab' fragment obtained by digesting the antibody obtained in Example 3 with pepsin and the subsequent reduction thereof, was labeled with peroxidase according to the maleimide hinge method (described in Enzyme Immunoassays, 3rd edition, published by Igakushoin). 150 µl of an antibody reaction solution (50 mM $Na_2PO_4$—$Na_2HPO_4$, 150 mM NaCl, pH 7.4, 2.0% Tween 20, 1% (w/v) normal rabbit serum, 0.067% (w/v) 4-aminoantipyrine) containing the resulting peroxidase-labeled antibody Fab' fragment at a concentration of 5 µg/ml was added to each of the wells and incubated at 4° C. for 2 hours. After the resulting antibody reaction solution was removed, each of the wells was washed 4 times with 300 µl of washing solution.

Then, 50 mM phosphate-25 mM citrate buffer (H 4.8) containing 1.0 mg/ml o-phenylene diamine and 0.017% (V/V) hydrogen peroxide was prepared just before use, and said buffer was added to the wells of the microtiter plate at a volume of 150 µl/well. Then, the microtiter plate was covered with aluminum foil and incubated at room temperature for 30 minutes. Thereafter, the reaction was terminated by adding 50 µl of 2 N sulfuric acid, and the coloration on the microtiter plate was measured for the difference of absorbance between the wavelengths of 492 nm and 595 nm in a multi-scanning spectrophotometer (Bio-Rad).

Diluted solutions of protein standard (I) prepared at concentrations of 0 to 100 ng/ml were used to prepare a calibration curve for the difference in absorbance for protein standard (I), and the concentration of the protein of the present invention in each of the test solutions was determined, based on the calibration curve.

Example 7

Confirmation (1) of the Correlation Between the Concentration of the Protein of the Present Invention and the Amount of Intraabdominal Adipose Tissue 200 µl of serum fractions were prepared by centrifuging (3,000×g, 10 minutes, 4° C.) blood samples from 100 persons and were used as control solutions. The concentration of the protein of the present invention in each of the resulting control solutions was determined by the method described in Example 5.

Figure 3:
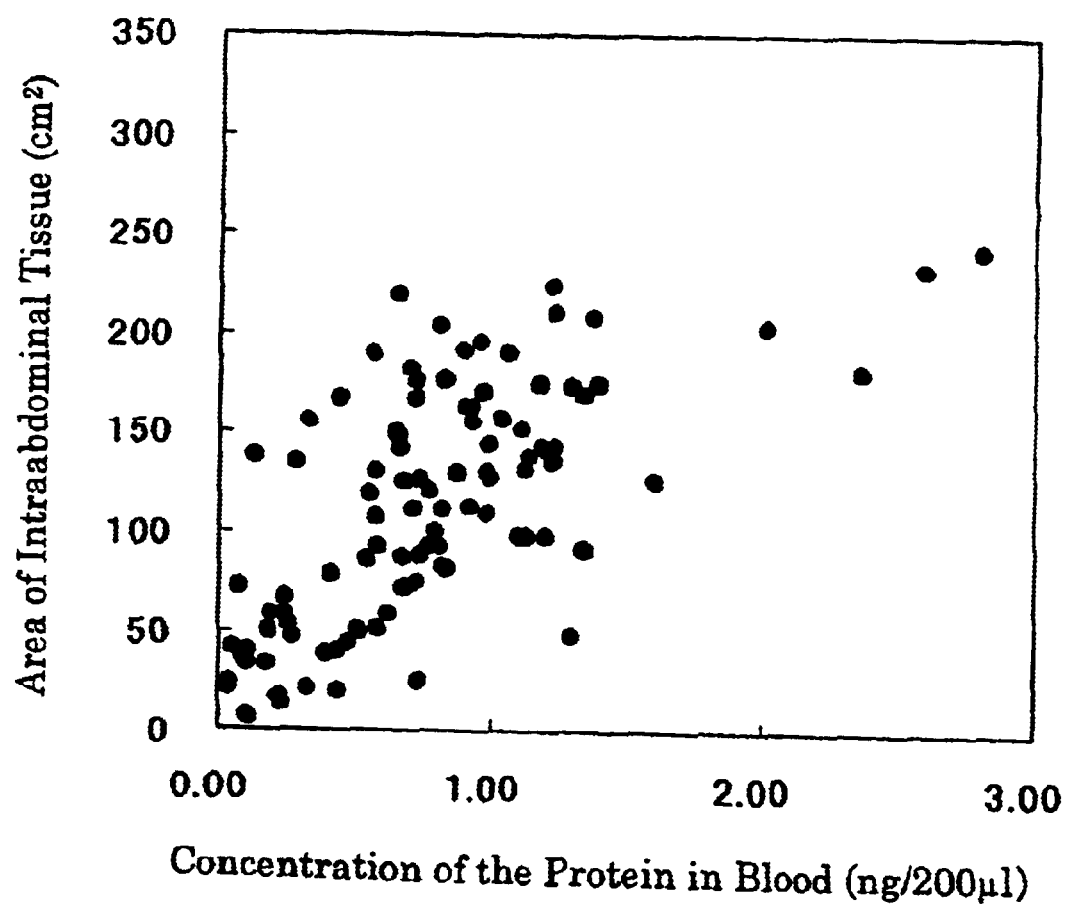
FIG. 3 is a drawing showing the correlation between the concentration (ng/200 µl) of a protein of the present invention in blood (X) and the area ($cm^2$) of intraabdominal adipose tissue (Y). Each plot is derived from a different individual.

The area of intraabdominal adipose tissue ($cm^2$) determined for each of the 100 persons by computed tomography of a section of the abdomen using CT scanning was plotted on the Y-axis and the concentration of the protein of the present invention (ng/200 µl) in each of the control solutions on the X-axis (FIG. 3). From the plots thereof, the coefficient of correlation between X and Y was determined to be about 0.7, and the correlation between X and Y, that is, Y=78.8X+ 51.4, was thus obtained.

Example 8

Figure 4:
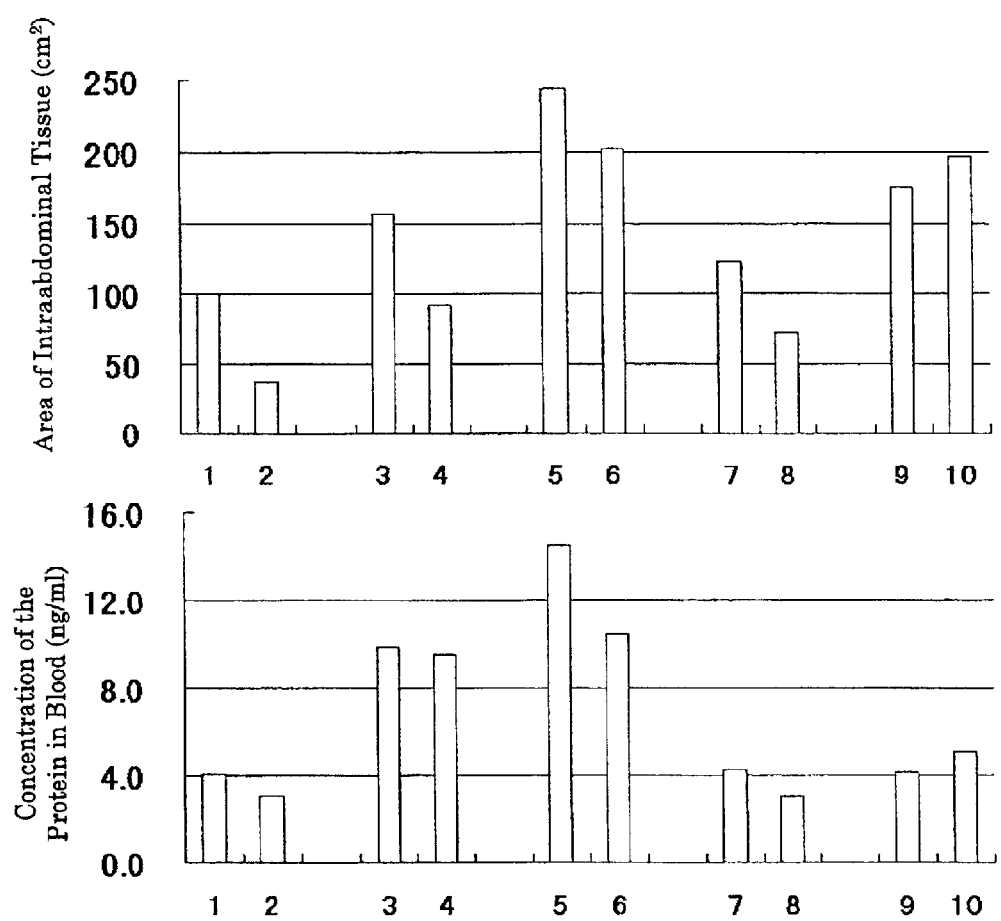
FIG. 4 shows a change in concentration of a protein of the present invention in blood from 5 examinees as determined by enzyme immunoassays before and after a predetermined period, as well as a change in the area of intraabdominal adipose tissue. Respectively, lane Nos. 1 and 2 indicate the results of examinee 1 before and after the predetermined period of 28 days; lane Nos. 3 and 4, the results of examinee 2 before and after the predetermined period of 49 days; lane Nos. 5 and 6, the results of examinee 3 before and after the predetermined period of 56 days; lane Nos. 7 and 8, the results of examinee 4 before and after the predetermined period of 63 days; and lane Nos. 9 and 10, the results of examinee 5 before and after the predetermined period of 17 days.

Confirmation (2) of the Correlation Between the Concentration of the Protein of the Present Invention and the Amount of Intraabdominal Adipose Tissue The concentration of the protein of the present invention in each blood sample from 5 examinees was measured before and after a predetermined period of time by the enzyme immunoassay described in Example 6. The changes in the concentration of the protein of the present invention before and after the predetermined period of time agreed with the changes in the area of intraabdominal fat determined, respectively, by tomography of a section of the abdomen by CT scanning before and after the predetermined period of time. That is, an examinee showing a reduction in the area of intraabdominal fat also showed a reduction in the concentration of the protein of the present invention in blood and an examinee showing an increase in the area of intraabdominal fat also showed an increase in the concentration of the protein of the present invention (FIG. 4).

Example 9

Measurement of the Protein of the Present Invention in Blood From Patients with Diseases Related Closely to an Increase in Intraabdominal Adipose Tissue The concentrations of the protein of the present invention in each blood sample collected from 38 patients with diabetes and 14 patients with coronary artery diseases were determined according to the method described in Example 5. The results are shown in Table 1.

TABLE 1

| Concentration of the protein of the present invention in blood | |
| --- | --- |
| Blood donors | Concentration of the protein of the present invention in blood (average; ng/ml) |
| Patients with diabetes | 14.7 |
| Patients with coronary artery diseases | 9.8 |

As illustrated hereinbefore, a method for analyzing the amount of intraabdominal adipose tissue, which is easily and rapidly feasible with satisfactory accuracy, can be provided according to the present invention.

What is claimed is:

1. A method for analyzing an amount of intraabdominal adipose tissue in a test animal comprising the steps of:
   (a) preparing a test solution comprising body fluids, tissue or cells of said test animal;
   (b) determining a concentration of a protein in the test solution, wherein the protein comprises
      (1) the amino acid sequence of SEQ ID NO:1, or
      (2) an amino acid sequence which is recognized by an antibody against a protein comprising the amino acid sequence of SEQ ID NO:1; and
   (c) determining the amount of intraabdominal adipose tissue in said test animal by comparing the concentration of protein from step (b) with an amount of said protein from a control animal having a known amount of intraabdominal adipose tissue, wherein said control animal is of the same species as the test animal.

2. The method according to claim 1 or 8, wherein the amount of intraabdominal adipose tissue corresponds to the area of intraabdominal adipose tissue in a section of the abdomen.

3. The method according to claim 1, wherein step (c) further comprises the steps of:
   (d) determining in advance a linear function which expresses a correlation between the amount of intraabdominal adipose tissue of the control animal and the concentration of the protein in a test solution comprising body fluids, tissue, or cells of said control animal; and
   (e) applying a value of the concentration of the protein of said test animal to the linear function determined in step (d) and calculating the amount of intraabdominal adipose tissue in the test animal.

4. The method according to claim 1 or 8, wherein the concentration of protein in the test solution is determined by an immunochemical analysis.

5. A method for determining an amount of intraabdominal adipose tissue in a test animal based upon a correlation between the amount of intraabdominal adipose tissue and a concentration of a protein in a test solution comprising body fluids, tissue or cells of the test animal, comprising the steps of:

(a) determining in advance a linear function which expresses a correlation between the amount of intraabdominal adipose tissue of a control animal and the concentration of the protein in a test solution comprising body fluids, tissues, or cells of the control animal; and (b) applying a value of the concentration of the protein of said test animal to the linear function determined in step (a) and calculating the amount of intraabdominal adipose tissue in said test animal, wherein the protein comprises
 (1) the amino acid sequence of SEQ ID NO:1, or
 (2) an amino acid sequence which is recognized by an antibody against a protein comprising the amino acid sequence of SEQ ID NO:1, and wherein said control animal is of the same species as the test animal.

6. The method according to claim 1 or 5, wherein the concentration of the protein in the test solution is determined by an immunochemical analysis.

7. The method according to claim 1, 5, or 8, wherein the test animal is a mammal.

8. A method for analyzing an amount of intraabdominal adipose tissue in a test animal comprising the steps of:

(a) preparing a test solution comprising blood of a test animal;

(b) determining a concentration of a protein in the test solution, wherein the protein comprises
 (1) the amino acid sequence of SEQ ID NO:1, or
 (2) an amino acid sequence which is recognized by an antibody against a protein comprising the amino acid sequence of SEQ ID NO:1; and (c) determining the amount of intraabdominal adipose tissue in said test animal by comparing the concentration of protein from step (b) with an amount of said protein from a control animal having a known amount of intraabdominal adipose tissue, wherein said control animal is of the same species as the test animal.

9. An examination method comprising:

predicting risk of onset of a disease closely related to an amount of intraabdominal adipose tissue or judging recovery of a disease in an individual of a test animal, based on examining the increasing or decreasing amount of intraabdominal adipose tissue of said individual for a predetermined period by the method of any one of claims 1 to 5 or 8.

10. An examination method comprising:

determining an amount of intraabdominal tissue in a test animal with a method of any one of claims 1 to 5 or 8;

comparing the amount of intraabdominal adipose tissue in said test animal to the amount of intraabdominal adipose tissue in a healthy animal of the same species; and predicting risk of onset of a disease closely related to an amount of intraabdominal adipose tissue or judging recovery of a disease in an individual of said test animal.

11. A kit comprising a protein as a standard for analyzing an amount of intraabdominal adipose tissue in an animal, wherein the protein comprises (1) the amino acid sequence of SEQ ID NO:1 or (2) an amino acid sequence which is recognized by an antibody against a protein comprising the amino acid sequence of SEQ ID NO:1.

12. The kit according to claim 11, further comprising an antibody which recognizes a protein comprising the amino acid sequence of SEQ ID NO:1.

13. The method according to claim 8, wherein step (c) further comprises the steps of:

(d) determining in advance a linear function which expresses a correlation between the amount of intraabdominal adipose tissue of the control animal and the concentration of the protein in a test solution comprising body fluids, tissue, or cells of said control animal; and (e) applying a value of the concentration of the protein of said test animal to the linear function determined in step (d) and calculating the amount of intraabdominal adipose tissue in the test animal.

* * * * *

SEQUENCE LISTING

<160> NUMBER OF SEQ ID NOS: 6

<210> SEQ ID NO 1
<211> LENGTH: 491
<212> TYPE: PRT
<213> ORGANISM: Homo sapiens

<400> SEQUENCE: 1

```
Met Asn Pro Ala Ala Glu Ala Glu Phe Asn Ile Leu Leu Ala Thr Asp
 1               5                  10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
    290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
            340                 345                 350
```

```
Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
    370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Lys Gly Arg Leu Ser Leu
            420                 425                 430

His Arg Thr Pro Ala Gly Asn Phe Val Thr Leu Glu Glu Gly Lys Gly
        435                 440                 445

Asp Leu Glu Glu Tyr Gly Gln Asp Leu Leu His Thr Val Phe Lys Asn
450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490

<210> SEQ ID NO 2
<211> LENGTH: 24
<212> TYPE: DNA
<213> ORGANISM: Artificial Sequence
<220> FEATURE:
<223> OTHER INFORMATION: Designed oligonucleotide primer to amplify
      antigen gene

<400> SEQUENCE: 2
ctgtcctccg gcccgagatg aatc                                          24

<210> SEQ ID NO 3
<211> LENGTH: 30
<212> TYPE: DNA
<213> ORGANISM: Artificial Sequence
<220> FEATURE:
<223> OTHER INFORMATION: Designed oligonucleotide primer to amplify
      antigen gene

<400> SEQUENCE: 3
cacaacacac acccagtcat aaagcctaat                                    30

<210> SEQ ID NO 4
<211> LENGTH: 27
<212> TYPE: DNA
<213> ORGANISM: Artificial Sequence
<220> FEATURE:
<223> OTHER INFORMATION: Designed oligonucleotide primer to amplify
      antigen gene

<400> SEQUENCE: 4
tataaacata tgccacccaa cacaagc                                       27

<210> SEQ ID NO 5
<211> LENGTH: 26
<212> TYPE: DNA
<213> ORGANISM: Artificial Sequence
<220> FEATURE:
<223> OTHER INFORMATION: Designed oligonucleotide primer to amplify
      antigen gene

<400> SEQUENCE: 5
cagtcaggat ccctaatgat gtgctg                                        26
```

-continued

```
<210> SEQ ID NO 6
<211> LENGTH: 1518
<212> TYPE: DNA
<213> ORGANISM: Homo sapiens
<220> FEATURE:
<221> NAME/KEY: CDS
<222> LOCATION: (18)..(1493)

<400> SEQUENCE: 6
ctgtcctccg gcccgag atg aat cct gcg gca gaa gcc gag ttc aac atc          50
                   Met Asn Pro Ala Ala Glu Ala Glu Phe Asn Ile
                    1               5                      10 ctc ctg gcc acc gac tcc tac aag gtt act cac tat aaa caa tat cca         98
Leu Leu Ala Thr Asp Ser Tyr Lys Val Thr His Tyr Lys Gln Tyr Pro
             15                  20                  25 ccc aac aca agc aaa gtt tat tcc tac ttt gaa tgc cgt gaa aag aag        146
Pro Asn Thr Ser Lys Val Tyr Ser Tyr Phe Glu Cys Arg Glu Lys Lys
 30                  35                  40 aca gaa aac tcc aaa tta agg aag gtg aaa tat gag gaa aca gta ttt        194
Thr Glu Asn Ser Lys Leu Arg Lys Val Lys Tyr Glu Glu Thr Val Phe
     45                  50                  55 tat ggg ttg cag tac att ctt aat aag tac tta aaa ggt aaa gta gta        242
Tyr Gly Leu Gln Tyr Ile Leu Asn Lys Tyr Leu Lys Gly Lys Val Val
 60                  65                  70                  75 acc aaa gag aaa atc cag gaa gcc aaa gat gtc tac aaa gaa cat ttc        290
Thr Lys Glu Lys Ile Gln Glu Ala Lys Asp Val Tyr Lys Glu His Phe
                 80                  85                  90 caa gat gat gtc ttt aat gaa aag gga tgg aac tac att ctt gag aag        338
Gln Asp Asp Val Phe Asn Glu Lys Gly Trp Asn Tyr Ile Leu Glu Lys
             95                  100                 105 tat gat ggg cat ctt cca ata gaa ata aaa gct gtt cct gag ggc ttt        386
Tyr Asp Gly His Leu Pro Ile Glu Ile Lys Ala Val Pro Glu Gly Phe
         110                 115                 120 gtc att ccc aga gga aat gtt ctc ttc acg gtg gaa aac aca gat cca        434
Val Ile Pro Arg Gly Asn Val Leu Phe Thr Val Glu Asn Thr Asp Pro
 125                 130                 135 gag tgt tac tgg ctt aca aat tgg att gag act att ctt gtt cag tcc        482
Glu Cys Tyr Trp Leu Thr Asn Trp Ile Glu Thr Ile Leu Val Gln Ser
140                 145                 150                 155 tgg tat cca atc aca gtg gcc aca aat tct aga gag cag aag aaa ata        530
Trp Tyr Pro Ile Thr Val Ala Thr Asn Ser Arg Glu Gln Lys Lys Ile
                 160                 165                 170 ttg gcc aaa tat ttg tta gaa act tct ggt aac tta gat ggt ctg gaa        578
Leu Ala Lys Tyr Leu Leu Glu Thr Ser Gly Asn Leu Asp Gly Leu Glu
             175                 180                 185 tac aag tta cat gat ttt ggc tac aga gga gtc tct tcc caa gag act        626
Tyr Lys Leu His Asp Phe Gly Tyr Arg Gly Val Ser Ser Gln Glu Thr
         190                 195                 200 gct ggc ata gga gca tct gct cac ttg gtt aac ttc aaa gga aca gat        674
Ala Gly Ile Gly Ala Ser Ala His Leu Val Asn Phe Lys Gly Thr Asp
 205                 210                 215 aca gta gca gga ctt gct cta att aaa aaa tat tat gga acg aaa gat        722
Thr Val Ala Gly Leu Ala Leu Ile Lys Lys Tyr Tyr Gly Thr Lys Asp
220                 225                 230                 235 cct gtt cca ggc tat tct gtt cca gca gca gaa cac agt acc ata aca        770
Pro Val Pro Gly Tyr Ser Val Pro Ala Ala Glu His Ser Thr Ile Thr
                 240                 245                 250 gct tgg ggg aaa gac cat gaa aaa gat gct ttt gaa cat att gta aca        818
Ala Trp Gly Lys Asp His Glu Lys Asp Ala Phe Glu His Ile Val Thr
             255                 260                 265
```

-continued

```
cag ttt tca tca gtg cct gta tct gtg gtc agc gat agc tat gac att      866
Gln Phe Ser Ser Val Pro Val Ser Val Val Ser Asp Ser Tyr Asp Ile
        270             275             280 tat aat gcg tgt gag aaa ata tgg ggt gaa gat cta aga cat tta ata      914
Tyr Asn Ala Cys Glu Lys Ile Trp Gly Glu Asp Leu Arg His Leu Ile
285             290             295 gta tcg aga agt aca cag gca cca cta ata atc aga cct gat tct gga      962
Val Ser Arg Ser Thr Gln Ala Pro Leu Ile Ile Arg Pro Asp Ser Gly
300             305             310             315 aac cct ctt gac act gtg tta aag gtt ttg gag att tta ggt aag aag     1010
Asn Pro Leu Asp Thr Val Leu Lys Val Leu Glu Ile Leu Gly Lys Lys
                320             325             330 ttt cct gtt act gag aac tca aag ggt tac aag ttg ctg cca cct tat     1058
Phe Pro Val Thr Glu Asn Ser Lys Gly Tyr Lys Leu Leu Pro Pro Tyr
            335             340             345 ctt aga gtt att caa ggg gat gga gta gat att aat acc tta caa gag     1106
Leu Arg Val Ile Gln Gly Asp Gly Val Asp Ile Asn Thr Leu Gln Glu
        350             355             360 att gta gaa ggc atg aaa caa aaa atg tgg agt att gaa aat att gcc     1154
Ile Val Glu Gly Met Lys Gln Lys Met Trp Ser Ile Glu Asn Ile Ala
365             370             375 ttc ggt tct ggt gga ggt ttg cta cag aag ttg aca aga gat ctc ttg     1202
Phe Gly Ser Gly Gly Gly Leu Leu Gln Lys Leu Thr Arg Asp Leu Leu
380             385             390             395 aat tgt tcc ttc aag tgt agc tat gtt gta act aat ggc ctt ggg att     1250
Asn Cys Ser Phe Lys Cys Ser Tyr Val Val Thr Asn Gly Leu Gly Ile
                400             405             410 aac gtc ttc aag gac cca gtt gct gat ccc aac aaa agg tcc aaa aag     1298
Asn Val Phe Lys Asp Pro Val Ala Asp Pro Asn Lys Arg Ser Lys Lys
            415             420             425 ggc cga tta tct tta cat agg acg cca gca ggg aat ttt gtt aca ctg     1346
Gly Arg Leu Ser Leu His Arg Thr Pro Ala Gly Asn Phe Val Thr Leu
        430             435             440 gag gaa gga aaa gga gac ctt gag gaa tat ggt cag gat ctt ctc cat     1394
Glu Glu Gly Lys Gly Asp Leu Glu Glu Tyr Gly Gln Asp Leu Leu His
445             450             455 act gtc ttc aag aat ggc aag gtg aca aaa agc tat tca ttt gat gaa     1442
Thr Val Phe Lys Asn Gly Lys Val Thr Lys Ser Tyr Ser Phe Asp Glu
460             465             470             475 ata aga aaa aat gca cag ctg aat att gaa ctg gaa gca gca cat cat     1490
Ile Arg Lys Asn Ala Gln Leu Asn Ile Glu Leu Glu Ala Ala His His
                480             485             490 tag gctttatgac tgggtgtgtg ttgtg                                     1518
```